US012559778B2

(12) United States Patent
Brichant et al.

(10) Patent No.: US 12,559,778 B2
(45) Date of Patent: Feb. 24, 2026

(54) METHOD FOR MAKING FRUCTOSE FROM GLUCOSE

(71) Applicant: NOVASEP PROCESS SOLUTIONS, Saint-Maurice-de-Beynost (FR)

(72) Inventors: Damien Brichant, Sarzeau (FR); Eric Valery, Lyons (FR)

(73) Assignee: NOVASEP PROCESS SOLUTIONS, Saint-Maurice-de-Beynost (FR)

( * ) Notice: Subject to any disclaimer, the term of this patent is extended or adjusted under 35 U.S.C. 154(b) by 1117 days.

(21) Appl. No.: 17/047,683

(22) PCT Filed: Apr. 22, 2019

(86) PCT No.: PCT/EP2019/060256
§ 371 (c)(1),
(2) Date: Oct. 14, 2020

(87) PCT Pub. No.: WO2019/206843
PCT Pub. Date: Oct. 31, 2019

(65) Prior Publication Data
US 2021/0164007 A1 Jun. 3, 2021

(30) Foreign Application Priority Data
Apr. 23, 2018 (EP) .................................... 18305502

(51) Int. Cl.
*C12P 19/02* (2006.01)
*A23L 5/20* (2016.01)
(Continued)

(52) U.S. Cl.
CPC .............. *C12P 19/02* (2013.01); *A23L 5/273* (2016.08); *A23L 5/49* (2016.08); *A23L 29/30* (2016.08);
(Continued)

(58) Field of Classification Search
CPC ....... A23L 5/273; A23L 5/49; B01D 15/1871; B01D 15/24; C12P 19/02; C12P 19/24
See application file for complete search history.

(56) References Cited

U.S. PATENT DOCUMENTS

| | | | |
|---|---|---|---|
| 4,366,060 A | 12/1982 | Leiser et al. | |
| 4,373,025 A | 2/1983 | Neuzil et al. | |

(Continued)

FOREIGN PATENT DOCUMENTS

| | | |
|---|---|---|
| CN | 101668867 A | 3/2010 |
| CN | 201801525 U | 4/2011 |

(Continued)

OTHER PUBLICATIONS

English Translation of CN 105177087 A. (Year: 2015).*

(Continued)

*Primary Examiner* — Stephanie A Kohler
(74) *Attorney, Agent, or Firm* — Hamilton, Brook, Smith & Reynolds, P.C.

(57) ABSTRACT

The invention relates to a method for producing a fructose composition comprising the following successive stages:
provision of an initial composition comprising glucose;
concentration of the initial composition by evaporation of water to obtain a concentrated initial composition;
isomerization of glucose to fructose from the concentrated initial composition, making it possible to obtain an intermediate composition;
purification of the intermediate composition in a multi-column chromatography system, making it possible to obtain a glucose-rich raffinate and a fructose-rich extract;
concentration of the extract by evaporation of water;

(Continued)

wherein the intermediate composition is not subjected to a concentration step by evaporation of water between the isomerization step and the purification step.

12 Claims, 2 Drawing Sheets

(51) Int. Cl.

| | | |
|---|---|---|
| *A23L 5/49* | (2016.01) |
| *A23L 29/30* | (2016.01) |
| *B01D 15/18* | (2006.01) |
| *B01D 15/42* | (2006.01) |
| *C12P 19/24* | (2006.01) |
| *C13K 11/00* | (2006.01) |

(52) U.S. Cl.
CPC ....... *B01D 15/1871* (2013.01); *B01D 15/426* (2013.01); *C12P 19/24* (2013.01); *C13K 11/00* (2013.01); *A23V 2002/00* (2013.01)

(56) References Cited

U.S. PATENT DOCUMENTS

| | | | |
|---|---|---|---|
| 5,221,478 A | 6/1993 | Dhingra et al. |
| 5,234,503 A | 8/1993 | Lillard, Jr. et al. |
| 9,441,280 B2 | 9/2016 | Pease et al. |
| 11,661,635 B2 | 5/2023 | Ebran et al. |
| 11,987,853 B2 | 5/2024 | Valery et al. |
| 2004/0231662 A1 | 11/2004 | De Mendonca Ferreira et al. |
| 2006/0273013 A1 | 12/2006 | Chin et al. |
| 2017/0304745 A1* | 10/2017 | Binder ................ B01D 15/185 |
| 2017/0307475 A1 | 10/2017 | Eyal et al. |
| 2021/0032711 A1 | 2/2021 | Valery et al. |
| 2021/0102266 A1 | 4/2021 | Ebran et al. |

FOREIGN PATENT DOCUMENTS

| | | | |
|---|---|---|---|
| CN | 102876758 A | 1/2013 |
| CN | 103060482 A | 4/2013 |
| CN | 104 630 312 A | 5/2015 |
| CN | 204625637 U | 9/2015 |
| CN | 105 177 087 A | 12/2015 |
| CN | 210826190 U | 6/2020 |
| FR | 2377827 | 8/1984 |
| FR | 2 668 775 A1 | 5/1992 |
| FR | 2 912 036 A1 | 8/2008 |
| WO | 92/07097 | 4/1992 |
| WO | 03/016577 A1 | 2/2003 |
| WO | 2014/030030 A1 | 2/2014 |
| WO | 2015/034643 A1 | 3/2015 |
| WO | 2015/104464 A1 | 7/2015 |
| WO | 2016/061037 A1 | 4/2016 |
| WO | 2019/206841 A1 | 10/2019 |
| WO | 2019/206842 A1 | 10/2019 |
| WO | 2019/206843 A1 | 10/2019 |

OTHER PUBLICATIONS

Nicoud, "Chromatographic Methods, Modeling, Simulation and Design," Cambridge University Press, 2015, p. 530-531.

PCT International Search Report for International Application No. PCT/EP2019/060255, entitled "Method For Chromatographic Purification Of Viscous Loads," Date of Mailing: Jul. 11, 2019, 15 pages.

International Search Report and Written Opinion for Int'l Application No. PCT/EP2019/060254, entitled "Fructose Purification Method", 13 pages, Date of Mailing: Jul. 11, 2019.

International Search Report and Written Opinion for International Application No. PCT/EP2019/060256, filed Apr. 22, 2019, entitled "Method For Making Fructose From Glucose", Date of Mailing: May 29, 2019, 13 pages.

Silva, et al., "Effect of Dead Volumes on the Performance of an Industrial-Scale Simulated Moving-Bed Parex Unit for p-Xylene Purification," AlChE Journal, vol. 62, No. 1, pp. 241-255 (Jan. 2016).

Notification of the First Office Action, issued for Chinese Application No. 201810870145.5, entitled "Method for Producing Fructose from Glucose," dated Oct. 14, 2022.

Chinese First Office Action, Appl. 201810871420.5 with English translation of Chinese First Office Action dated Mar. 15, 2022.

* cited by examiner

METHOD FOR MAKING FRUCTOSE FROM GLUCOSE

This application is the U.S. National Stage of International Application No. PCT/EP2019/060256, filed Apr. 22, 2019, which designates the U.S., published in French, and claims priority under 35 U.S.C. § 119 or 365 (c) to European Application No. 18305502.9, filed Apr. 22, 2018. The entire teachings of the above applications are incorporated herein by reference.

SCOPE OF THE INVENTION

The present invention relates to a method for producing a fructose composition from an initial composition comprising glucose, as well as an installation adapted to the implementation of this method.

TECHNICAL BACKGROUND

In the food industry, there is a significant use of fructose-based compositions especially known under the designation HFS for "High Fructose Syrup". In particular, under the designation HFS 55 is known a composition comprising about 55% by mass of fructose relative to the total dry matter, and under the designation HFS 95 is known a composition comprising at least 95% by mass of fructose relative to the total dry matter.

It is known to manufacture the compositions HFS 55 and HFS 95 by isomerization from a glucose-based composition. Traditionally, the manufacturing method includes a first evaporation to concentrate the glucose-based composition, then an isomerization step, then another evaporation to carry out a second concentration, then a chromatographic purification making it possible to separate a fructose-enriched flow from a glucose-enriched flow, and another evaporation to carry-out a third concentration from the fructose-enriched flow.

This method requires a relatively heavy installation and involves significant energy consumption.

There is thus a need to produce fructose-based compositions, such as the composition HFS 55 or the composition HFS 95 with greater efficiency (and for example with lower energy consumption) and/or with reduced chromatography column dimensions.

SUMMARY OF THE INVENTION

The invention relates, according to a first possible definition, to a method for producing a fructose composition comprising the following successive steps:
provision of an initial composition comprising glucose;
concentration of the initial composition by evaporation of water to obtain a concentrated initial composition;
isomerization of glucose to fructose from the concentrated initial composition, making it possible to obtain an intermediate composition;
purification of the intermediate composition in a multi-column chromatography system, making it possible to obtain a glucose-rich raffinate and a fructose-rich extract;
concentration of the extract by evaporation of water;
wherein the intermediate composition is not subjected to a concentration step by evaporation of water between the isomerization step and the purification step.

The invention also relates, independently of the foregoing and according to a second possible definition, to a method for producing a fructose composition comprising the following successive steps:
provision of an initial composition comprising glucose;
concentration of the initial composition by evaporation of water to obtain a concentrated initial composition;
isomerization of glucose to fructose from the concentrated initial composition, making it possible to obtain an intermediate composition;
purification of the intermediate composition in a multi-column chromatography system, making it possible to obtain a glucose-rich raffinate and a fructose-rich extract;
concentration of the extract by evaporation of water;
the mass concentration of dry matter of the intermediate composition at the end of the isomerization step being equal to the mass concentration of dry matter of the intermediate composition subjected to the purification step within 5%.

In what follows, the term "method of the invention" is understood to mean the above-mentioned method, regardless of the first or the second definition.

In certain embodiments, the method of the invention further comprises a step of removing residual color from the extract prior to the concentration step of the extract, preferably by ion exchange resin and/or by activated carbon as well as, preferably, by a sterile filtration step.

In some embodiments, the method of the invention further comprises a demineralization step between the isomerization step and the chromatography step.

In some embodiments of the method of the invention, the purification is carried out at a temperature greater than or equal to 50° C., preferably 55 to 65° C., and more preferably about 60° C.

In some embodiments of the method of the invention, the raffinate is recycled and added to the initial composition prior to the concentration step of the initial composition.

In some embodiments of the method of the invention:
the initial composition has a dry matter mass concentration of 25 to 35%, preferably about 31%; and/or
the concentrated initial composition has a dry matter mass concentration greater than or equal to 40%; and/or
the intermediate composition comprises at least 40% by mass of fructose relative to the total dry matter; and/or
the produced fructose composition has a dry matter mass concentration greater than or equal to 75%, preferably about 77%.

In some embodiments of the method of the invention, the intermediate composition which is subjected to the purification step has a dry matter mass concentration of 45 to 55%, and preferably about 50%.

In some embodiments of the method of the invention:
the produced fructose composition contains a mass proportion of fructose, relative to the total dry matter, greater than or equal to 95%, preferably greater than or equal to 98%; or
a part of the intermediate composition is collected prior to the purification step and added to the extract prior to the concentration step of the extract, the produced fructose composition preferably containing a mass proportion of fructose, relative to the total dry matter from 50 to 60%, more preferably from 54 to 56%; and the mass ratio of the part of the intermediate composition collected from the total intermediate composition preferably being from 0.4 to 0.6, more preferably from 0.45 to 0.55, preferably from 0.48 to 0.52.

In some embodiments of the method of the invention, the dry matter mass concentration of the intermediate composition varies from less than 5%, and preferably remains essentially constant, between the end of the isomerization step and the beginning of the purification step.

In certain embodiments of the method of the invention, the multicolumn chromatography system comprises from 4 to 6 cells; and/or comprises columns having a length of 1.0 to 2.6 m, preferably 1.4 to 2.0 m.

In some embodiments, the method of the invention comprises the injection of water as an eluent in the purification step, and:

the ratio of the mass flow rate of eluent to the mass flow rate of dry matter of the produced fructose composition, is from 0.5 to 1.3, preferably from 0.6 to 1.2; and/or the injected volume of eluent is from 0.12 to 0.24 BV.

In some embodiments of the method of the invention, the volume of intermediate composition subjected to the purification step is from 0.13 to 0.40 BV.

In some embodiments of the method of the invention, the intermediate composition subjected to the purification step contains a mass proportion of fructose greater than 42%.

In certain embodiments of the method of the invention, the multicolumn chromatography system comprises a plurality of columns and intercolumn fluidic links, and the velocity of the fluids in the intercolumn fluidic links is greater than 0.5 m/s, preferably greater than 1 m/s, and more preferably greater than 1.5 m/s.

In some embodiments, a portion of the intermediate composition is added to the extract prior to concentrating it.

In some embodiments, the method is devoid of any evaporation step other than that of concentrating the initial composition and that of concentrating the extract.

The invention also relates to an installation for producing a fructose composition comprising:

a feed line of an initial composition comprising glucose;

a first evaporator fed by the feed line of initial composition;

a collection line of concentrated initial composition at the outlet of the first evaporator;

an isomerization reactor of glucose to fructose fed by the collection line of concentrated initial composition;

a collection line of intermediate composition at the outlet of the isomerization reactor;

a multicolumn chromatography system fed by the collection line of intermediate composition;

a collection line of raffinate and a collection line of extract at the outlet of the multi-column chromatography system;

a second evaporator fed by a feed line coming from the collection line of extract;

a collection line of fructose composition at the outlet of the second evaporator;

wherein the collection line of intermediate composition does not feed an evaporator.

In some embodiments, the installation comprises a unit for discoloration of the extract located between the multi-column chromatography system and the second evaporator, preferably comprising a bed of ion exchange resin and/or activated carbon, as well as preferably, a sterile filtration unit.

In some embodiments, the installation comprises a demineralization unit between the isomerization reactor and the multicolumn chromatography system.

In some embodiments, the collection line of raffinate is connected to the feed line of initial composition in order to feed the first evaporator.

In some embodiments, the installation comprises a bypass line of intermediate composition from the collection line of intermediate composition and connected to the collection line of extract in order to feed the second evaporator through the feed line.

In some embodiments, the multicolumn chromatography system comprises from 4 to 6 cells; and/or comprises columns having a length of 1.0 to 2.6 m, preferably 1.4 to 2.0 m.

In some embodiments, the multicolumn chromatography system comprises a plurality of columns and inter-column fluidic links, and the volume of the intercolumn fluidic links is less than 10%, preferably less than 5%, and preferably less than 3% of the volume of the columns.

In some embodiments, the installation does not include an evaporator other than the first evaporator and the second evaporator.

The present invention makes it possible to meet the need expressed in the prior art. More particularly, it provides a method and an installation for producing a fructose-based composition, such as a HFS 55 or a HFS 95 composition, more efficiently.

This is accomplished due to the use of only two evaporation steps, and due to the elimination of the evaporation step between isomerization and chromatographic purification; or maintaining a substantially constant dry matter mass concentration between the isomerization step and the chromatographic purification step.

Surprisingly, the present inventors have discovered that the use of an input feedstock to the chromatographic purification less concentrated than in the prior art improves the efficiency of the method. In particular, the invention makes it possible to reduce the volume of consumed eluent (and therefore the energy consumption), and/or to reduce the volume of stationary phase used, and/or to increase the volume of feedstock to be treated, and/or to reduce the size of the chromatographic columns, and, if necessary, with a more compact and less expensive production installation.

DESCRIPTION OF EMBODIMENTS OF THE INVENTION

The invention will now be described in more detail and without limitation in the description which follows.

Comparative Method

For the sake of simplicity, a comparative method for the production of fructose composition is first described, relative to which the method of the invention constitutes an improvement.

Figure 1:
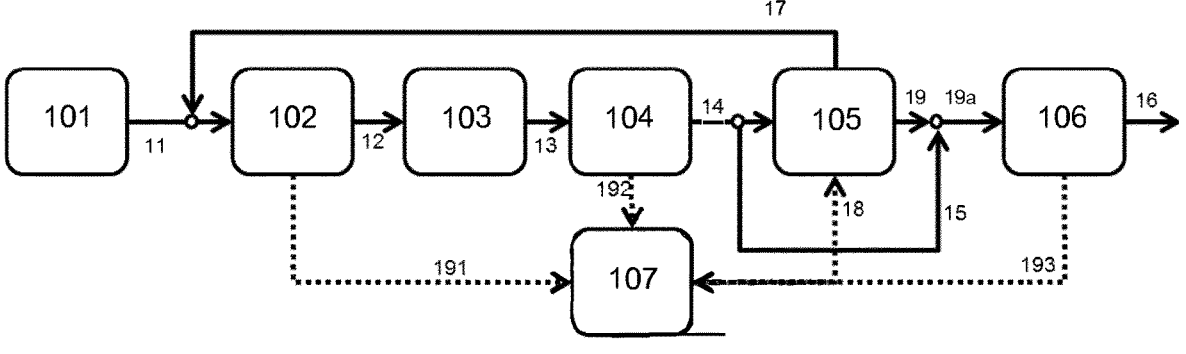
FIG. 1 schematically shows a comparative installation (which is not according to the invention).

Making reference to FIG. 1, an installation for implementing a comparative method for producing fructose composition comprises the following elements:

a source 101 of initial composition comprising glucose;

a first evaporator 102 fed by a feed line of initial com-
position comprising glucose 11 coming from the source
101 of initial composition comprising glucose;

a collection line of concentrated initial composition 12 at
the outlet of the first evaporator 102;

an isomerization reactor 103 fed by the collection line of
concentrated initial composition 12;

a collection line of intermediate composition 13 at the
outlet of the isomerization reactor 103;

a second evaporator 104 fed by the collection line of
intermediate composition 13;

a collection line of concentrated intermediate composition
14 at the outlet of the second evaporator 104;

a multicolumn chromatography system 105 fed by the
collection line of concentrated intermediate composi-
tion 14 as well as by a line of eluent 18;

a collection line of extract 19 and a collection line of
raffinate 17 from the multicolumn chromatography
system 105, the raffinate collection line 17 ensuring
recycling towards the feed line of initial composition
11;

a third evaporator 106 fed by a feed line 19a, itself fed by
the collection line of extract 19;

a collection line of fructose composition 16 at the outlet
of the third evaporator 106;

a first purge line 191, a second purge line 192 and a third
purge line 193 respectively at the outlets of the first
evaporator 102, the second evaporator 104 and the third
evaporator 106; and a bypass line of concentrated intermediate composition 15
coming from the collection line of concentrated inter-
mediate composition 14 and directly feeding the feed
line 19a (in combination with the collection line of
extract 19) upstream of the third evaporator 106. Alter-
natively, one or more intermediate devices may be
arranged on line 15. By way of example, a buffer tank
may be provided for storing the intermediate compo-
sition.

Thus, according to the comparative method, an initial
composition comprising glucose, first undergoes a concen-
tration step in the first evaporator 102, at the end of which
a concentrated initial composition is recovered. This is
brought to the isomerization reactor 103, in which part of the
glucose is converted to fructose in an isomerization step. At
the outlet of the isomerization reactor 103, a so-called
intermediate composition is recovered. This intermediate
composition undergoes a concentration step in the second
evaporator 104, at the end of which a concentrated inter-
mediate composition is recovered. This is brought to the
multicolumn chromatographic system 105, which is sepa-
rately fed with eluent, namely water.

A chromatographic purification is carried out in the mul-
ticolumn chromatographic system 105, at the outlet of which
an extract and a raffinate are recovered. The raffinate is
enriched in glucose relative to the intermediate composition,
while the extract is enriched in fructose. The raffinate is
recycled by combining it with the initial composition before
the first concentration step. The extract is combined with a
portion of the concentrated intermediate composition in
order to adjust the fructose concentration to a desired
content, and then this flow is subjected to a concentration
step in the third evaporator 106, at the end of which the
desired fructose composition is recovered.

Water 107 is recovered from the first purge line 191, the
second purge line 192 and the third purge line 193, and is
used as eluent source for the multicolumn chromatographic system 105 or as any other source of water that may be used
in the installation or nearby unit operations.

General Presentation of the Method of the Invention

Compared to the above comparative method, the inven-
tion advantageously provides for the elimination of the
concentration step between the isomerization and the chro-
matographic purification, and therefore the elimination of
the second evaporator. The third evaporator in the compara-
tive method thus becomes the second evaporator in the
invention.

Figure 2:
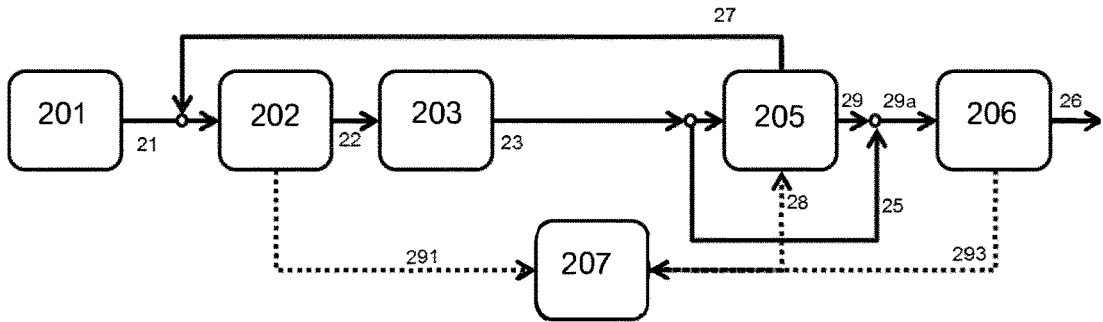
FIG. 2 schematically shows an embodiment of an installation according to the invention.

Thus, making reference to FIG. 2, an example of an
installation for implementing the method for producing a
fructose composition may comprise the following elements:

a source 201 of initial composition comprising glucose;

a first evaporator 202 fed by a feed line of initial com-
position comprising glucose 21 coming from the source
201 of initial composition comprising glucose;

a collection line of concentrated initial composition 22 at
the outlet of the first evaporator 202;

an isomerization reactor 203 fed by the collection line of
concentrated initial composition 22;

a collection line of intermediate composition 23 at the
outlet of the isomerization reactor 203;

a multicolumn chromatography system 205 fed by the
collection line of intermediate composition 23 as well
as by a line of eluent 28;

a collection line of extract 29 and a collection line of
raffinate 27 coming from the multicolumn chromatog-
raphy system 205, the raffinate collection line 27
optionally providing recycling to the feed line of initial
composition 21;

a second evaporator 206 fed by a feed line 29a, itself fed
by the collection line of extract 29;

a collection line of fructose composition 26 at the outlet
of the second evaporator 206;

a first purge line 291 and a second purge line 293
respectively at the outlets of the first evaporator 202
and the second evaporator 206; and optionally, a bypass line of intermediate composition 25
coming from the collection line of intermediate com-
position 23 and directly feeding the feed line 29a (in
combination with the collection line of extract 29)
upstream of the second evaporator 206. Alternatively,
one or more intermediate devices may be arranged on
the line 25. By way of example, a buffer tank may be
provided for storing the intermediate composition.

Thus, according to the method of the invention, an initial
composition comprising glucose first undergoes a concen-
tration step in the first evaporator 202, at the end of which
a concentrated initial composition is recovered. This is
brought to the isomerization reactor 203, in which part of the
glucose is converted to fructose in an isomerization step.
The isomerization of glucose to fructose is not complete. At
the outlet of the isomerization reactor 203, a so-called
intermediate composition is recovered. This is brought to the
multicolumn chromatographic system 205, which is sepa-
rately fed with eluent, namely water.

A chromatographic purification is carried out in the mul-
ticolumn chromatographic system 205, at the outlet of which
an extract and a raffinate are recovered. The raffinate is
enriched in glucose relative to the intermediate composition,
while the extract is enriched in fructose. The raffinate is
optionally recycled by combining it with the initial compo-
sition before the first concentration step.

The extract may be combined with a portion of the
intermediate composition in order to adjust the fructose
concentration to a desired content, and then this flow is subjected to a concentration step in the second evaporator 206, at the end of which the desired fructose composition is recovered. This is particularly useful when it is desired to obtain a low final purity in fructose (e.g. composition of the type HFS 55).

Alternatively, and contrary to what is illustrated in the figure, the extract may be directly subjected to the concentration step in the second evaporator 206, at the end of which the desired fructose composition is recovered, without combining it with another flow. This is particularly useful when it is desired to obtain a high final purity in fructose (e.g. composition of the type HFS 95).

In the context of the production of high purity fructose, the bypass line of intermediate composition 25 of FIG. 2 may be omitted and the collection line of raffinate 27 may allow recycling to saccharification and/or demineralization units upstream of the source 201. In order to avoid the concentration of the polysaccharides as a result of this recycling, a nanofiltration unit or a chromatographic separation unit may be placed for example in this collection line of raffinate 27 in order to eliminate the polysaccharides.

The mass ratio of the intermediate composition part that is optionally collected (in the bypass line of intermediate composition 25) (and optionally combined with the extract) relative to the total intermediate composition (in the collection line of intermediate composition 23) may notably be from 0.4 to 0.6, preferably from 0.45 to 0.55, more preferably from 0.48 to 0.52, in particular when the fructose mass content of the total intermediate composition is close to 42%. This mass ratio may, in particular, be from 0.45 to 0.65, preferably from 0.50 to 0.65, more preferably from 0.57 to 0.61, in particular when the fructose mass content of the intermediate composition total is close to 44%.

The water 207 is recovered from the first purge line 291 and the second purge line 293. This recovered water may be used as the eluent source for the multicolumn chromatographic system 205; alternatively, fresh water may be used in whole or in part for the eluent.

Preferably, a demineralization step (not shown in the figure) may be carried out between the isomerization step 203 and the chromatography step 205. The demineralization system thus comprises columns filled with ion exchange resin, cationic and/or anionic, as a stationary phase.

Preferably, a step of removing the residual color of the extract (or discoloration) is carried out prior to the concentration of the extract in the second evaporator 206. This may be carried out by arranging a bleaching unit (not shown in the figure) between the multicolumn chromatography system 205 and the second evaporator 206. The discoloration may comprise the passage of the extract flow on a cationic and/or anionic ion exchange resin and/or on a bed of activated carbon in the form of powder or grains. Sterile filtration may be associated with this step.

The first evaporator 202 and the second evaporator 206 may be plate or tubular, single effect or multiple effect, single-pass or recirculation, steam or mechanical vapor recompression, with or without a thermocompressor.

The isomerization reaction is preferably an enzymatic reaction. An enzyme such as isomerase is put in contact with the product in a reactor, preferably at a temperature between 50 and 60° C., preferably at a pH between 7 and 8. Enzymes such as Novozymes Sweetzyme® or Gensweet® from Gencor may be used for this operation.

The method of the invention is preferably continuous.

Preferably, the intermediate composition obtained at the end of the isomerization step does not undergo a concentration step by evaporation of water prior to the chromatographic purification step. In other words, no evaporator is provided between the isomerization reactor 203 and the multicolumn chromatography system 205.

It is possible that the collection line of intermediate composition 23 directly connects the isomerization reactor 203 to the multicolumn chromatography system 205 without any intermediate devices. Alternatively, one or more intermediate devices may be arranged between the isomerization reactor 203 and the multicolumn chromatography system 205. By way of example, a buffer tank may be provided for storing the intermediate composition.

Preferably, the dry matter mass concentration of the intermediate composition at the inlet of the multicolumn chromatography system 205 is equal to the dry matter mass concentration of the intermediate composition at the outlet of the isomerization reactor 203, if necessary to within ±5%, within ±4%, or within ±3%, or within ±2%, or within ±1%, or exactly.

The above tolerance is expressed as percentages of dry matter. To take an example, if a composition has a dry matter mass concentration of 50% within ±5%, it means that the composition has a dry matter mass concentration of 45 to 55%.

It is possible to envisage, for example, a slight dilution of the intermediate composition before the multicolumn chromatography system 205, for example by a supply of water. However, it is preferred for more simplicity that no active adjustment of the dry matter mass concentration of the intermediate composition is made between the isomerization reactor 203 and the multicolumn chromatography system 205.

Compositions

The initial composition used in the method of the invention comprises glucose. It is preferably an aqueous composition. It is preferably a glucose syrup with a so-called high dextrose level. It preferably has a dry matter mass concentration of 25 to 35%, preferably 28 to 33%, and more preferably about 31%.

In general, the dry matter mass concentration of a composition corresponds to the mass of dry matter of the composition relative to the total mass thereof. In the compositions used in the invention, the dry matter mass concentration is approximately equal to the sugar content in Brix degrees.

The initial composition used in the method of the invention preferably contains a mass proportion of glucose (relative to the dry matter) greater than or equal to 50%, or 80%, or 90%. More preferably, it contains a mass proportion of glucose of about 95%. Preferably, the rest of the dry matter is mainly composed of polysaccharides.

After the concentration step, the concentrated initial composition is obtained. It has essentially the same composition in sugars as the initial composition, but it has a higher dry matter mass concentration, for example from 40 to 58%, preferably from 45 to 55%, more preferably from 48 to 52%. and more preferably about 50%.

The intermediate composition, which is obtained at the end of the isomerization, also comprises a dry matter mass concentration, for example 40 to 58%, preferably 45 to 55%, more preferably 48 to 52%, and more preferably about 50%. Preferably, the dry matter mass concentration of the intermediate composition at the end of the isomerization is substantially identical to the dry matter mass concentration of the concentrated initial composition.

During the isomerization step, a part of the glucose is converted to fructose. In certain embodiments, the intermediate composition contains a mass proportion of glucose (relative to the dry matter) from 40 to 65%, preferably from 45 to 60%, more preferably from 50 to 55% and, for example, about 53%. In certain embodiments, the intermediate composition contains a mass proportion of fructose (relative to the dry matter) from 30 to 55%, preferably from 35 to 50%, more preferably from 40 to 45% and, for example, about 42%. In certain embodiments, the intermediate composition contains a mass proportion of polysaccharides (relative to the dry matter) from 1 to 10%, preferably from 3 to 8%, more preferably from 4 to 6% and, for example, from about 5%.

In some embodiments, the intermediate composition contains a mass proportion of fructose greater than 42% and less than 45%, and for example a mass proportion of fructose of about 43% or about 44%. It has in fact been found that the change from a mass proportion of fructose of 42% to 43% makes it possible to improve the indicators of water consumption and resin volume requirements of the order of 7 to 9%. The mass proportion of fructose in the intermediate composition may be adjusted by modifying the operating conditions of the isomerization reaction (duration, for example).

At the end of the chromatographic purification, a fructose-enriched extract is obtained and thus depleted in glucose, and a glucose-enriched raffinate and thus depleted in fructose.

By "enriched" fraction in one species A and "depleted" in one species B, is meant that the ratio of species A/species B molar concentrations in the fraction is greater than that of the input flow of the chromatographic purification (independently of the effects of concentration or overall dilution).

In some embodiments, the recovered fructose composition (obtained after concentrating the extract in the collection line of the fructose composition 26) has a dry matter mass concentration of at least 75%, preferably of at least 76%, for example about 77%.

In some embodiments, the recovered fructose composition contains a mass proportion of glucose (based on dry matter) from 35 to 48%, preferably from 38 to 45%, more preferably from 39 to 42%, for example about 40%. In some embodiments, the recovered fructose composition contains a mass proportion of fructose (based on dry matter) from 50 to 60%, preferably from 52 to 58%, more preferably from 54 to 56%, for example about 55%. In some embodiments, the recovered fructose composition contains a mass proportion of polysaccharides (based on dry matter) from 2 to 8%, preferably from 3 to 7%, more preferably from 4 to 6%, for example about 5%.

In other embodiments, the recovered fructose composition contains a mass proportion of fructose (relative to dry matter) greater than or equal to 95%, preferably 96%, more preferably 97%, more preferably 98%, more preferably 98.5%.

Preferably, at least 80% by mass of the fructose contained in the mixture to be separated is recovered in the extract, more preferably at least 90% by mass.

Chromatographic Purification

The chromatographic purification is carried out in an assembly of several chromatography columns containing a stationary phase, with successively and cyclically, in a given part of the system:

a step of collecting a raffinate, a step of injecting the mixture to be separated, a step of collecting an extract and a step of mobile phase injection.

The various steps above follow one another temporally in one part of the system. The part of the system in question is preferably located between the outlet of one column and the inlet of the next column. Alternatively, the part of the system in question may include a column or part of a column.

At a given instant, one or more of the above steps may be simultaneously implemented in one or more parts of the system. For example, all of these steps may be simultaneously implemented in respective parts of the system.

The "mixture to be separated" or "feedstock" or "feedstock to be treated" is the mixture containing a product of interest (in this case, fructose) which is subjected to the chromatographic purification. The purification is meant to enrich a fraction (in this case, the extract) in said product of interest.

By "raffinate" is meant the fraction obtained by elution which contains the species that are relatively least retained by the stationary phase, and therefore whose elution is the fastest.

By "extract" is meant the fraction obtained by elution which contains the species that are relatively most retained by the stationary phase, and therefore whose elution is the slowest.

The eluent is a fluid injected to displace the species retained by the stationary phase. In the invention, the eluent used is preferably water.

By "mobile phase" is meant the fluid that displaces in the columns of the system. Depending on its position, each column is traversed by a mobile phase volume depending on the zone in which the column is located, wherein this volume may be different from the volume of eluent which is injected into one or another of the columns. In the case of a multicolumn method with identified zones between the input and output lines (as described in more detail below), the term "mobile phase volume" designates the volume of fluid which enters a zone. This fluid may be different from the eluent in the strict sense, but it contributes to the displacement of the products in each column of the zone. This is referred to as the mobile phase volume associated with each zone. The preferred configuration of the zones in the chromatographic system is described in more detail hereafter.

In certain advantageous embodiments, the chromatographic system comprises sequencing members of the injection and collection lines. In particular, the sequencing of these injection and collection lines takes place over an operating cycle of the system. In the present application, an "operating cycle" or "cycle" designates the time at the end of which the injection and collection lines have been sequenced until they return to their initial position in the system. At the end of a cycle, the system is back to its original configuration. A cycle generally comprises as many "periods" as columns. Thus the cycle of a method implemented on an 8-column system is composed of 8 successive periods.

The unit BV ("Bed Volume") makes it possible to measure the volume of mobile phase flowing in each zone (or of injected eluent, or of injected feedstock to be treated), relative to the volume of stationary phase bed in a column. The measurement of these volumes is per period.

The stationary phase used in the invention is preferably a divalent strong cationic resin in calcium form, having a particle size (Dv50) comprised between 100 and 600 μm, preferably between 170 and 400 μm.

The chromatographic purification of the invention is implemented in a multicolumn chromatographic system. Preferably, the chromatographic system comprises from 4 to 10 columns.

Preferably, the chromatographic purification of the invention is carried out continuously.

Preferably, the chromatographic purification of the invention is a periodic chromatographic accumulation method.

By "accumulation method" is meant a chromatographic method in which the injection of the mixture to be separated (starting flow) is intercalated or added to a non-zero concentration profile passing from the outlet to the inlet of a column.

Examples of such accumulation methods are AMB, SMB, VariCol, Powerfeed, ModiCon, iSMB or SSMB methods.

The simulated moving bed (or SMB for "simulated moving bed") method is a continuous multicolumn method, wherein the injection of the mixture to be separated being carried out over an entire cycle.

The SMB method may, notably, be a four-zone SMB method. In this case, the system comprises a set of columns connected in series and in closed loop, the output of a column being connected to an inlet of a next column. The system comprises at least one injection line for the mixture to be separated, a collection line of a raffinate, an injection line of an eluent and a collection line of an extract. The injection lines (flow and eluent) and the collection lines of the fractions are displaced periodically and synchronously (synchronous sequencing) within the loop in the direction of the flow of the fluid circulating through the loop. The duration between two offsets of the assembly of the injection and collection lines of a column corresponds to a period; at the end of a cycle, all the points have returned to their initial position, the system having a cyclic operation. A cycle has as many periods as columns.

An AMB (or actual moving bed) system has a similar operation to an SMB system. However, instead of moving the injection points of the feedstock flow and eluent, as well as collection points, by means of a valve system, a set of adsorption units (columns) are moved physically relative to the feeding and collection points. Again, the operation makes it possible to simulate a continuous moving bed against the current.

The chromatographic purification of the invention may be a continuous injection method of the mixture to be separated (i.e. a method in which the injection of the mixture to be separated is a continuous flow). The injection of the mixture to be separated is thus carried out throughout the cycle. The chromatographic purification of the invention may also be a quasi-continuous injection method of the mixture to be separated.

Alternatively, the chromatographic purification of the invention may be a method in which the injection of the mixture to be separated (starting flow) is discontinuous. In these methods, the injection of the mixture to be separated is not carried out over an entire cycle, but for a total duration of less than one cycle. A discontinuous injection method of the mixture to be separated is the iSMB ("improved simulated moving bed") method described in documents EP 0342629 and U.S. Pat. No. 5,064,539, to which reference is expressly made, may be mentioned. In this method, in one-step the system operates in a closed loop, without injection or product collection.

The sequential simulated moving bed or SSMB ("sequential simulated moving bed") method is another preferred example. An SSMB system cuts out the introductions and collections of the flows into sub-sequences applied in periodic ways. An SSMB system is, for example, described in the document WO 2015/104464.

Preferably, the chromatographic purification of the invention is a method of the SSMB type.

The chromatographic system preferably comprises zones 1, 2, 3 and 4: zone 1 is located between an injection line of an eluent and a collection line of the extract; zone 2 is located between the collection line of the extract and an injection line of the mixture to be separated; zone 3 is located between the injection line of the mixture to be separated and a collection line of the raffinate; and zone 4 is located between the collection line of the raffinate and the injection line of an eluent.

Figure 3:
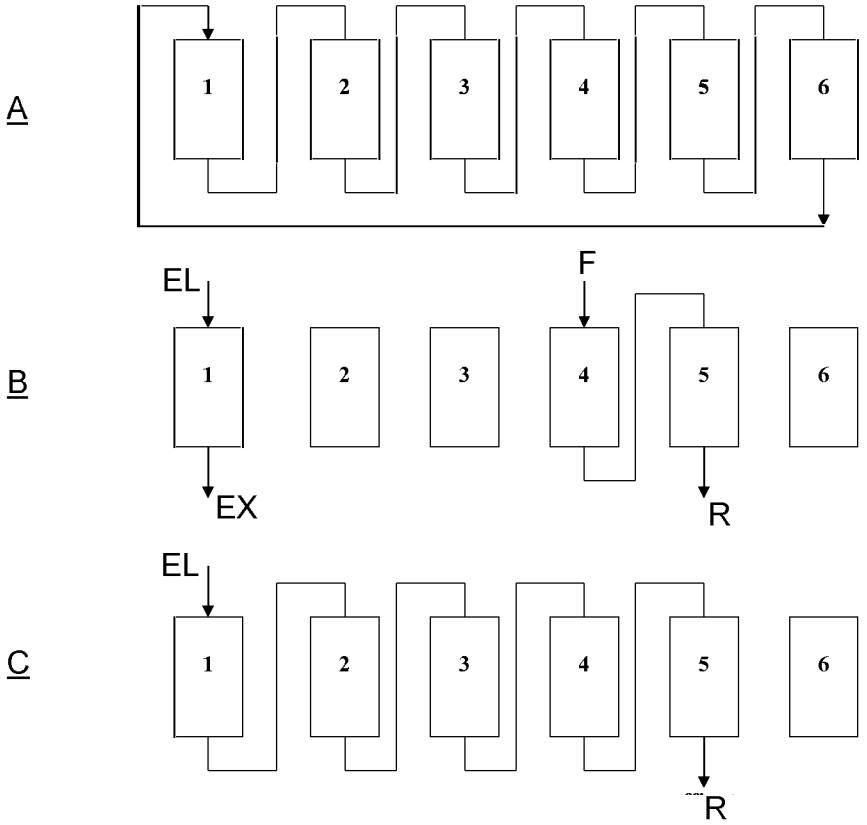
FIG. 3 schematically shows an SSMB chromatographic system that may be used to implement the method of the invention.

A possible example of an SSMB system that may be used in the invention is shown with reference to FIG. 3. In this example, six cells or columns are used. This system may be operated according to a cyclic operation in four phases.

Phase 1 (part A of the figure): loop phase, during which a continuous closed loop circulation is maintained on all the cells placed in series, to displace the interstitial volume of one cell to the next, without the injection of eluent. The skilled in the art will note that the volume of mobile phase displaced in this phase contributes to zones 1, 2, 3 and 4.

Phase 2 (part B of the figure): feedstock/injection of feedstock. The feedstock flow (F) is injected at the top of the fourth cell. Simultaneously, a substantially identical volume of raffinate (R) is collected at the outlet of the fifth cell. The cells 4 and 5 here constitute zone 3. The cells 2 and 3 constitute the separation zone between the extract and the feedstock injection. They constitute zone 2 here. The skilled in the art will note that the volume of mobile phase displaced in this phase contributes to zone 3.

Phase 3 (part B of the figure): elution of the extract. The eluent (EL) is injected onto the first cell to elute the extract (EX), which is collected in a substantially identical volume at the bottom of the first cell. The cell No. 1 here constitutes zone 1. The skilled in the art will note that the volume of mobile phase displaced in this phase contributes to zone 1.

Phases 2 and 3 are preferably operated simultaneously to increase the productivity of the system.

Phase 4 (part C of the figure): elution of the raffinate. The eluent (EL) is injected at the top of the first cell, and the raffinate (R) is collected in a substantially identical volume out of the fifth. Cell No. 6 is here a buffer cell allowing to ensure the separation between the tail of the extract and the head of the raffinate. It constitutes zone 4. This zone may be omitted in the case where the degree of purity and/or the desired yield is relatively limited. The skilled in the art will note that the volume of mobile phase displaced in this phase contributes to zones 1, 2 and 3.

These phases are operated in the order of 1 to 4 in a preferred embodiment. Their sequence constitutes a complete sequence (also called period).

Each sequence (phases 1 to 4) is repeated six times by shifting the cell inputs and outputs by incrementing the cell number, from the left to the right of the system: the feedstock is thus injected at the top of cell No. 1 in sequence No. 1, then at the top of cell No. 2 in sequence No. 2, etc.

A complete production cycle is carried out after completion of the six successive sequences, when the injection point of the feedstock, initially at the input of cell No. 1, returns again to the input of cell No. 1.

In the foregoing, a description of the SSMB system has been given with reference to the case where the cells correspond to columns. This is not limiting, and the invention also applies to systems in which the cells, or even compartments, are parts of the column.

Moreover, the number of columns present in zones 1, 2, 3 and 4 may vary according to the desired quality of separation. Therefore, systems of the same type with a cell, two cells, three cells, four cells, five cells, six cells, and up to twelve cells or more may also be designed.

The columns may have notably a length of 1 to 2.6 m, namely: from 1.0 to 1.2 m, or from 1.2 to 1.4 m, or from 1.4 to 1.6 m, or from 1.6 to 1.8 m, or from 1.8 to 2.0 m, or from 2.0 to 2.2 m, or from 2.2 to 2.4 m, or from 2.4 to 2.6 m; a range of 1.4 to 2.0 m is considered preferable. The length in question is the useful length of the column, corresponding to the height of the stationary phase bed in the column.

As described above and as illustrated in the examples below, the invention makes it possible to improve the performance of the chromatographic installation.

However, performance losses may be encountered during a change of scale of the installation. In particular, when the diameter of the columns exceeds about one meter in diameter, it may be crucial to control the dead volumes.

The dead volumes correspond to the total (internal) volume of the "inter-column fluidic links", i.e. the links between the output or outputs of a column and the input or inputs of the next column. Any element located between two successive columns, such as a pipe (or conduit), a valve or a pump, belongs to the inter-column fluidic links. Volumes found after a collection valve of an extract or raffinate, or before injection valves are not considered as dead volumes (volumes located between the chromatography system and storage tanks for the feedstock to be injected, eluent, extract and raffinate).

It is advantageous for the velocity of the fluids flowing in the inter-column fluidic connections, and, in particular, in the pipes or conduits thereof, to exceed 0.5 m/s, preferably 1 m/s and more preferably 1.5 m/s. The fluid velocity considered here is the average velocity (flow divided by the cross section).

The control of the velocity in the inter-column fluidic links is carried out, for example, by adjusting the diameter of these links for a given flow rate.

When treating a relatively viscous mixture to be separated, using relatively small fluidic connection diameters leads to an increase in the velocity of the fluids, but also in the pressure in the installation. Therefore, the search for a good fluid velocity/fluid viscosity pair requires optimization work. In the context of the separation of glucose and fructose, as described above, the fluid velocities given above have been found to be adequate.

It is also advantageous if the total volume of the inter-column fluidic links is less than 10% of the total volume of the columns, preferably less than 5%, or even 3% of the total volume of the columns. This makes it possible to avoid a drop in the performance of up to one or two points of purity or efficiency. The adjustment of these dead volumes may be carried out by minimizing the total length of the inter-column fluidic links (notably pipes or conduits).

Preferably, the fluid velocity and dead volume values above are associated with columns having a diameter greater than or equal to 1 m (useful diameter, or diameter of the stationary phase bed in the columns).

Setting the Chromatographic Purification

The fluid flow rates in the different columns of the chromatographic system may be adjusted in order to obtain the following operating parameters.

The ratio of the mass flow rate of eluent to the mass flow rate of dry matter of produced fructose composition may be from 0.5 to 0.6; or from 0.6 to 0.7; or from 0.7 to 0.8; or from 0.8 to 0.9; or from 0.9 to 1.0; or from 1.0 to 1.1; or from 1.1 to 1.2; or from 1.2 to 1.3. Ranges from 0.5 to 1.3, especially 0.6 to 1.2, are examples of preferred ranges.

The injected volume of eluent may be, notably, from 0.12 to 0.14 BV; or from 0.14 to 0.16 BV; or from 0.16 to 0.18 BV; or from 0.18 to 0.20 BV; or from 0.20 to 0.22 BV; or from 0.22 to 0.24 BV.

The volume of feedstock to be treated (volume of intermediate composition subjected to the chromatographic purification step) may be notably from 0.13 to 0.16 BV; or from 0.16 to 0.18 BV; or from 0.18 to 0.20 BV; or from 0.20 to 0.22 BV; or from 0.22 to 0.24 BV; or from 0.24 to 0.26 BV; or from 0.26 to 0.28 BV; or from 0.28 to 0.30 BV; or from 0.30 to 0.32 BV; or from 0.32 to 0.34 BV; or from 0.34 to 0.36 BV; or from 0.36 to 0.38 BV; or from 0.38 to 0.40 BV.

The chromatographic purification is preferably carried out at a temperature greater than or equal to 50° C.; and in notably: from 50 to 53° C.; or from 53 to 55° C.; or from 55 to 58° C., or from 58 to 60° C.; or from 60 to 62° C.; or from 62 to 65° C.; or from 65 to 70° C. A temperature of about 60° C. is an example of a particularly suitable temperature. The above temperature corresponds to the average temperature of the mobile phase in the chromatographic system.

EXAMPLES

The following examples illustrate the invention without limiting it. In all the examples, a chromatographic purification system of the SSMB type was used. The system comprises four columns filled with Novasep Process resin XA2004-30Ca or XA2004-31Ca as a stationary phase, over a bed height of two meters in each column.

The respective volumes of mobile phase in zones 1, 2, 3 and 4 are denoted by $BV_1$, $BV_2$, $BV_3$ and $BV_4$. In the examples below, the volume of eluent (denoted $BV_{water}$ and equal to $BV_1 - BV_4$) is adjusted in a range from 0.11 to 0.25. The volume of feedstock to be treated (denoted $BV_{feed}$ and equal to $BV_3 - BV_2$) is adjusted in a range from 0.11 to 0.30. The flow rates $BV_1$ and $BV_2$ are scanned in the following ranges: from 0.65 to 0.75 and from 0.55 to 0.65. The volumes $BV_3$ and $BV_4$ are calculated as follows: $BV_3 = BV_2 + BV_{feed}$ and $BV_4 = BV_1 - BV_{water}$.

The adjustments of $BV_1$ and $BV_2$ fluctuate from one system to another for reasons of stationary phase density variability. On the other hand, this variability does not have any impact on the performances due to the volume of water and the load volume used.

For each adjustment performed, purities and yields are measured experimentally, but the purities and yields are not in themselves significant in characterizing the invention. In fact, regardless of the fructose purity of the extract obtained at the chromatography outlet, a partial mixture with the non-enriched mixture is carried out before the final evaporation.

For clarity reasons, the following examples directly show the material balance results corresponding to the best settings obtained. The tables correspond to a daily production of 250 tons of fructose HFS 55 in dry matter composition, which corresponds to 310 tons of liquid HFS 55 at 77% dry matter. The performance of the chromatography is evaluated according to the $t_{water}/t_{HFS}$ ratios (the mass ratio of the daily water flow rate used on the daily dry matter flow rate of the produced fructose composition) and $V_{CHR}/t_{HFS}$ (the ratio of the stationary phase volume in the installation brought back to the mass of dry matter fructose composition produced per day).

Example 1 (Comparative)

This reference example is implemented according to the schematic of FIG. 1 described above (installation with three evaporators, and inlet flow of the chromatographic unit having a dry matter mass concentration of 60%).

In this example, the volume of water (eluent) used ($BV_{water}$) is equal to 0.177 BV and the volume of feedstock to be treated ($BV_{feed}$) is equal to 0.2 BV. The following table summarizes the characteristics of the compositions passing in different lines of the installation. The flow is indicated in metric tons per day. The dry matter level is indicated as a mass percentage relative to the total mass of the composition in question. The fructose, glucose and polysaccharide levels are indicated in mass percentages relative to the dry matter of the composition in question.

| Line | 11 | 12 | 13 | 14 | 15 | 16 | 18 | 193 |
|---|---|---|---|---|---|---|---|---|
| Flow rate | 807 | 694 | 694 | 578 | 296 | 326 | 194 | 326 |
| Dry matter | 31% | 50% | 50% | 60% | 60% | 77% | 0 | 0 |
| Fructose | 0% | 2% | 42% | 42% | 42% | 55% | — | — |
| Glucose | 95% | 92% | 52% | 52% | 52% | 40% | — | — |
| Polysac-charides | 5% | 6% | 6% | 6% | 6% | 5% | — | — |

In this example, the $t_{water}/t_{HFS}$ ratio is equal to 0.78. The $V_{CHR}/t_{HFS}$ ratio is equal to 0.35 m$^3$/t.

Example 2 (Invention)

This example is implemented according to the schematic of FIG. 2 described above (installation with two evaporators, and inlet flow of the chromatographic unit having a dry matter mass concentration of 50%).

In this example, the volume of water (eluent) used is equal to 0.15 BV and the volume of feedstock to be treated is equal to 0.25 BV. The following table summarizes the characteristics of the compositions passing in different lines of the installation, in the same manner as in Example 1.

| Line | 21 | 22 | 23 | 25 | 26 | 28 | 293 |
|---|---|---|---|---|---|---|---|
| Flow rate | 807 | 788 | 788 | 358 | 326 | 194 | 326 |
| Dry matter | 31% | 50% | 50% | 50% | 77% | 0 | 0 |
| Fructose | 0% | 7% | 42% | 42% | 55% | — | — |
| Glucose | 95% | 88% | 53% | 53% | 40% | — | — |
| Polysaccharides | 5% | 5% | 5% | 5% | 5% | — | — |

In this example, the $t_{water}/t_{HFS}$ ratio is equal to 0.77. The $V_{CHR}/t_{HFS}$ ratio is equal to 0.3 m$^3$/t.

Compared with Example 1, it appears that despite a drop in the concentration of the product at the inlet of the chromatography (from 60 to 50% of dry matter), while decreasing the total volume of elution water and increasing the one of the batch to be treated, the volume of resin per ton of final product is lower.

Example 3 (Invention)

This example is similar to Example 2, except that the volume of water used is equal to 0.14 BV and that the volume of feedstock to be treated is equal to 0.27 BV. The following table summarizes the characteristics of the compositions passing in different lines of the installation, in the same way as in the preceding examples:

| Line | 21 | 22 | 23 | 25 | 26 | 28 | 293 |
|---|---|---|---|---|---|---|---|
| Flow rate | 807 | 782 | 782 | 358 | 326 | 178 | 326 |
| Dry matter | 31% | 50% | 50% | 50% | 77% | 0 | 0 |
| Fructose | 0% | 7% | 42% | 42% | 55% | — | — |
| Glucose | 95% | 88% | 53% | 53% | 40% | — | — |

-continued

| | | | | | | |
|---|---|---|---|---|---|---|
| Polysaccharides | 5% | 5% | 5% | 5% | 5% | — | — |

In this example, the $t_{water}/t_{HFS}$ ratio is equal to 0.71. The ratio $V_{CHR}/t_{HFS}$ ratio is equal to 0.32 m$^3$/t. This example demonstrates that if the volume of elution water is further lowered, while also increasing the volume of feedstock to be treated (compared to Example 2), the volume of resin per ton of final product is a little superior but the performance obtained on the volume of water per ton of final product remains very advantageous.

Example 4 (Invention)

This example is similar to Example 2, except that the volume of water used is equal to 0.14 BV and that the volume of feedstock to be treated is equal to 0.17. In addition, the length of columns is reduced to 1.40 m instead of the 2 m in the previous examples. The following table summarizes the characteristics of the compositions passing in different lines of the installation, in the same way as in the preceding examples:

| Line | 21 | 22 | 23 | 25 | 26 | 28 | 293 |
|---|---|---|---|---|---|---|---|
| Flow rate | 807 | 700 | 700 | 341 | 326 | 264 | 326 |
| Dry matter | 31% | 50% | 50% | 50% | 77% | 0 | 0 |
| Fructose | 0% | 3% | 42% | 42% | 55% | — | — |
| Glucose | 95% | 91% | 52% | 52% | 40% | — | — |
| Polysaccharides | 5% | 6% | 6% | 6% | 5% | — | — |

In this example, the $t_{water}/t_{HFS}$ ratio is equal to 0.96. The $V_{CHR}/t_{HFS}$ ratio is equal to 0.27 m$^3$/t. This example demonstrates that it is possible to work with shorter columns while maintaining good productivity, which makes it possible to obtain good performance in water consumption and particularly optimized with respect to resin requirements. Other settings may be found to lower the water consumption for larger resin volumes.

What is claimed is:

1. A method for producing a fructose composition comprising the following successive steps:

provision of an initial composition comprising glucose;

concentration of the initial composition by evaporation of water to obtain a concentrated initial composition;

isomerization of glucose to fructose from the concentrated initial composition, making it possible to obtain an intermediate composition;

purification of the intermediate composition in a multi-column chromatography system, making it possible to obtain a glucose-rich raffinate and a fructose-rich extract;

concentration of the extract by evaporation of water;

wherein the intermediate composition is not subjected to a concentration step by evaporation of water between the isomerization step and the purification step, and wherein the purification step includes injection of water as an eluent, the ratio of the mass flow rate of eluent to the mass flow rate of dry matter of the produced fructose composition, being from 0.5 to 1.3, wherein the raffinate is recycled and added to the initial composition prior to the concentration of the initial composition step, wherein a part of the intermediate composition is added to the extract before concentrating it, wherein the volume of intermediate composition subjected to the purification step is from 0.13 to 0.40 BV, and wherein the ratio of the injected volume of eluent to the volume of intermediate composition subjected to the purification step is 0.885 or less.

2. The method of claim 1, further comprising a step of removing residual color from the extract prior to the concentration of the extract step.

3. The method of claim 1, further comprising a demineralization step between the isomerization step and the purification step.

4. The method of claim 1, wherein the purification is carried out at a temperature greater than or equal to 50° C.

5. The method of claim 1, wherein the intermediate composition which is subjected to the purification step has a dry matter mass concentration of 45 to 55%.

6. The method of claim 1, wherein the dry matter mass concentration of the intermediate composition varies by less than 5%, between the end of the isomerization step and the beginning of the purification step.

7. The method of claim 1, wherein the multicolumn chromatography system comprises a plurality of columns and intercolumn fluidic links, and wherein the velocity of the fluids in the intercolumn fluidic links is greater than 0.5 m/s.

8. The method of claim 1, wherein the method is devoid of any evaporation step other than that of concentrating the initial composition and that of concentrating the extract.

9. The method of claim 1,
the injected volume of eluent being from 0.12 to 0.24 BV.

10. A method for producing a fructose composition comprising the following successive steps:
provision of an initial composition comprising glucose;
concentration of the initial composition by evaporation of water to obtain a concentrated initial composition;
isomerization of glucose to fructose from the concentrated initial composition, making it possible to obtain an intermediate composition;
purification of the intermediate composition in a multi-column chromatography system, making it possible to obtain a glucose-rich raffinate and a fructose-rich extract;
concentration of the extract by evaporation of water;
the mass concentration of dry matter of the intermediate composition at the end of the isomerization step being equal to the mass concentration of dry matter of the intermediate composition subjected to the purification step within 5%, and
the purification includes injection of water as an eluent, the ratio of the mass flow rate of eluent to the mass flow rate of dry matter of the produced fructose composition, being from 0.5 to 1.3, wherein the raffinate is recycled and added to the initial composition prior to the concentration of the initial composition step, wherein a part of the intermediate composition is added to the extract before concentrating it, wherein the volume of intermediate composition subjected to the purification step is from 0.13 to 0.40 BV, and wherein the ratio of the injected volume of eluent to the volume of intermediate composition subjected to the purification step is 0.885 or less.

11. A method for producing a fructose composition comprising the following successive steps:

provision of an initial composition comprising glucose;
concentration of the initial composition by evaporation of water to obtain a concentrated initial composition;
isomerization of glucose to fructose from the concentrated initial composition, making it possible to obtain an intermediate composition;
purification of the intermediate composition in a multi-column chromatography system, making it possible to obtain a glucose-rich raffinate and a fructose-rich extract;
concentration of the extract by evaporation of water;
wherein the intermediate composition is not subjected to a concentration step by evaporation of water between the isomerization step and the purification step, and
wherein the purification step includes injection of water as an eluent, the ratio of the mass flow rate of eluent to the mass flow rate of dry matter of the produced fructose composition, being from 0.5 to 1.3, and the method further comprises a step of removing residual color from the extract prior to the concentration of the extract step, wherein a part of the intermediate composition is added to the extract before concentrating it, wherein the volume of intermediate composition subjected to the purification step is from 0.13 to 0.40 BV, and wherein the ratio of the injected volume of eluent to the volume of intermediate composition subjected to the purification step is 0.885 or less.

12. A method for producing a fructose composition comprising the following successive steps:
provision of an initial composition comprising glucose;
concentration of the initial composition by evaporation of water to obtain a concentrated initial composition;
isomerization of glucose to fructose from the concentrated initial composition, making it possible to obtain an intermediate composition;
purification of the intermediate composition in a multi-column chromatography system, making it possible to obtain a glucose-rich raffinate and a fructose-rich extract;
concentration of the extract by evaporation of water;
wherein the intermediate composition is not subjected to a concentration step by evaporation of water between the isomerization step and the purification step, and
wherein the purification step includes injection of water as an eluent, the ratio of the mass flow rate of eluent to the mass flow rate of dry matter of the produced fructose composition, being from 0.5 to 1.3, and wherein the multicolumn chromatography system comprises a plurality of columns and intercolumn fluidic links, wherein the velocity of the fluids in the intercolumn fluidic links is greater than 0.5 m/s, wherein a part of the intermediate composition is added to the extract before concentrating it, wherein the volume of intermediate composition subjected to the purification step is from 0.13 to 0.40 BV, and wherein the ratio of the volume of intermediate composition subjected to the purification step to the injected volume of eluent is 0.885 or less.

* * * * *